United States Patent [19]
Selby et al.

[11] Patent Number: 6,096,505
[45] Date of Patent: Aug. 1, 2000

[54] NONCLONING TECHNIQUE FOR EXPRESSING A GENE OF INTEREST

[75] Inventors: Mark Selby, San Francisco; Kent B. Thudium; Dino Dina, both of Oakland, all of Calif.

[73] Assignee: Chiron Corporation, Emeryville, Calif.

[21] Appl. No.: 09/290,449

[22] Filed: Apr. 13, 1999

Related U.S. Application Data

[60] Provisional application No. 60/081,777, Apr. 14, 1998.

[51] Int. Cl.$^7$ .............................. C12Q 1/68; C12P 21/00; C12N 15/63; C12N 5/00; C07H 21/04
[52] U.S. Cl. .......................... 435/6; 435/69.1; 435/320.1; 435/325; 435/455; 536/23.1; 536/24.1
[58] Field of Search ........................... 435/6, 69.1, 320.1, 435/325, 455; 536/23.1, 24.1

[56] References Cited

U.S. PATENT DOCUMENTS 4,710,463  12/1987  Murray .

FOREIGN PATENT DOCUMENTS

WO94/24301  10/1994  WIPO .

OTHER PUBLICATIONS

Penolazzi et al. Direct transfection of polymerase chain reactoin generated DNA fragments into mammalian cells employing ethidium bromide inidcator and ultrafiltration. Anal. Biochem. vol. 248:190–193, Feb. 1997.

Campbell, et al. Homologous recombinatino involving small single–stranded oligonucleotides in human cells. The New Biologist. vol. 1(2):223–237, Nov. 1989.

Malpiece et al. Coloniy hybridization method for screening si situ of eukaryotic amplified genes. Experientia. Vo. 40:483–485, Mar. 1984.

Song et al. Effect or double–strand breaks on homologous recombination in mammalian cells and extracts. Mol. and Cellular Biol. vol. 5(12):3331–3336, Dec. 1985.

He et al. Construction of adenoviral and retroviral vectors coexpressing the genes encoding the hepatitis B surface antigen and B7–1 protein. Gene vol. 175:121–125, Nov. 1996.

Blázquez et al., "Mutations in the aphA–2 Gene of Transposon Tn5 Mapping Within the Regions Highly Conserved in Arminoglyoside–Phosphotransferases Strongly Reduce Aminoglycoside Resistance," *Molecular Microbiology* 5(6):1511–1518 (1991).

Escher and Schaffner, "Improved "Activator Trap" Method for the Isolation of Transcriptional Activation Domains From Random DNA Fragments," *Biotechniques* 1:848–854 (1996).

Gurtu et al., "IRES Bicistronic Expression Vectors for Efficient Creation of Stable Mammalian Cell Lines," *Biochemical and Biophysical Research Communications* 229:295–298 (1996).

Herlitschka et al., "Overexpression of Human Prothrombin in Permanent Cell Lines Using a Dominant Selection/Amplification Fusion Marker," *Protein Expression and Purification* 8:358–364 (1996).

Kaufman et al., "Improved Vectors for Stable Expression of Foreign Genes in Mammalian Cells by Use of the Untranslated Leader Sequence From EMC Virus," *Nucleic Acids Research* 19(16)4485–4490 (1991).

Kobayashi et al., "Improved Dicistronic mRNA Expression Vectors for Efficient Selection of Transfectants highly Expressing Foreign Genes," *Bio Techniques* 21:398–402 (1996).

Mosser et al., "Use of a Dicistronic Expression Cassette Encoding the Green Fluorescent Protein for the Screening and Selection of Cells Expressing Inducible Gene Products," *Bio Techniques* 22:150–161 (1997).

Penolazzi et al., "Direct Transfection of Polymerase Chain Reaction–Generated DNA Fragments into Mammalian Cells Employing Ethidium Bromide Indicator and Ultrafiltration," *Analytical Biochemistry* 248:190–193 (1997).

Rees et al., "Bicistronic Vector for the Creation of Stable Mamalian Cell Lines that Predisposes All Antibiotic–Resistant Cells to Express Recombinant Protein," *Bio Techniques* 20:102–110 (1996).

*Primary Examiner*—Robert A. Schwartzman
*Assistant Examiner*—William Sandals
*Attorney, Agent, or Firm*—Roberta L. Robins; Alisa A. Harbin; Robert P. Blackburn

[57] ABSTRACT

A noncloning method for expressing a gene of interest in a mammalian host cell is disclosed. The invention utilizes three basic individual elements: (1) a promoter element; (2) at least one gene of interest; and (3) a selectable marker cassette which includes in 5' to 3' order, an internal ribosome entry site ("IRES"), at least one gene coding for a selectable marker, and a transcription termination sequence. The three individual elements are cotransfected into a mammalian host cell where they become operably linked such that expression of the selectable marker gene(s) necessarily requires coexpression of the gene of interest.

36 Claims, 6 Drawing Sheets

NONCLONING TECHNIQUE FOR EXPRESSING A GENE OF INTEREST

CROSS-REFERENCE TO RELATED APPLICATION

This application is related to provisional patent application Ser. No. 60/081,777, filed Apr. 14, 1998, from which priority is claimed under 35 USC §119(e)(1) and which is incorporated herein by reference in its entirety.

TECHNICAL FIELD

The present invention relates generally to genetic engineering and recombinant protein production techniques. In particular, the invention relates to a noncloning method for expressing a gene of interest in a mammalian host cell.

BACKGROUND OF THE INVENTION

Recombinant technology provides an attractive method for producing proteins of high purity in large quantities. Conventional techniques for recombinantly producing proteins in eukaryotes require that the gene of interest be first inserted into an expression plasmid, in vitro, prior to transfection of a host cell. The expression plasmid includes a promoter, which allows RNA polymerase to specifically bind to the DNA sequence in order to initiate transcription. A polyadenylation signal may also be present. A selectable marker is used to allow the identification of host cells which express the gene of interest.

Standard techniques for transfecting host cells require the use of two separate expression cassettes, one bearing the gene of interest driven by an appropriate promoter, and the other including a selectable marker driven by a separate promoter. These cassettes may be present in a single plasmid or may be delivered to the host cell using separate vectors. However, such techniques may result in reduced recoveries of clones containing the gene of interest due to deletion or inactivation of the cassette expressing the same. Alternatively, if separate vectors are used, constructs including only the selectable marker and not the gene of interest, may be stably integrated into the host cell genome. Thus, background effects may be seen caused by false positive clones carrying only the marker plasmid and not the gene of interest.

More recently, expression constructs have been developed which include one or more selectable markers, in addition to the gene of interest, under the control of a single promoter. Such constructs are referred to in the art as "dicistronic" or "bicistronic." For example, constructs have been developed which include an internal ribosome entry site known as "IRES" derived from, e.g., the encephalomyocarditis virus (EMCV). The IRES element permits the translation of two or more open reading frames from a single messenger RNA, one encoding the recombinant protein of interest and the other encoding the selectable marker. See, e.g., Kaufman et al., *Nuc. Acids Res.* (1991) 19:4485–4490; Gurtu et al., *Biochem. Biophys. Res. Comm.* (1996) 229:295–298; Rees et al., *BioTechniques* (1996) 20:102–110; Kobayashi et al., *BioTechniques* (1996) 21:399–402; and Mosser et al., *BioTechniques* (1997 22 150–161.

Although the use of a single expression cassette decreases the number of false positives, the technique requires that the gene of interest be first subcloned into an expression cassette including a promoter, prior to use. If the expression of multiple genes is desired, such as from a cDNA library, the technique is particularly cumbersome, time-consuming and labor-intensive. Accordingly, there is a continued need for improved methods for producing proteins recombinantly.

Penolazzi et al., *Anal. Biochem.* (1997) 248:190–193, describe the direct transfection of PCR-generated DNA fragments, labeled with ethidium bromide (EtdBr), into mammalian cells. The cells were reported to retain the EtdBr-DNA for 48 hours.

Escher, D. and Schaffner, W., *BioTechniques* (1996) 21:848–854, describe a system where a linearized recipient vector containing a yeast GAL4 DNA binding domain (DBD) under the control of a CMV promoter, and an SV40 origin of replication, is cotransfected into a recipient mammalian cell with a fragmented DNA including a potential activation domain. The technique is said by the authors to produce functional fusion proteins by in vivo ligation of the components.

However, none of the aforementioned references describes a noncloning system whereby a promoter element, a gene of interest, and a selectable marker are individually cotransfected into a mammalian cell to result in expression of the protein encoded by the gene of interest.

DISCLOSURE OF THE INVENTION

Accordingly, the present invention is based on the discovery of a noncloning method for producing a recombinant protein. The system of the invention eliminates the need to subclone the gene of interest into an expression cassette prior to use and therefore provides a desirable method for producing a recombinant protein and a particularly convenient method for expressing several recombinant proteins, e.g., from a cDNA library. Moreover, the noncloning technique described herein allows for the direct use of a PCR product (either known or unknown), the direct use of synthetic DNA, as well as the direct use of DNA derived from a DNA virus or other organism. Thus, the method provides for rapid expression of a gene of interest in mammalian cells.

In addition, the system is designed such that expression of one or more selectable marker genes is under the control of the same promoter that drives expression of the gene of interest. Thus, the gene of interest and selectable marker are transcribed as a dicistronic message, reducing the problem of false positive clones, described above.

In particular embodiments, the present invention also advantageously makes use of an attenuated marker gene which confers reduced resistance to a toxic molecule. Greater amounts of the selectable marker must therefore be expressed in order to overcome the weaker resistance conferred by the gene. Hence, cells selected based on expression of the marker may inherently contain higher levels of the recombinant product.

Additionally, the system of the present invention is designed such that an IRES sequence is present upstream of the selectable marker gene. One advantage of structuring the system in this way is that those sequences downstream of the IRES elements, i.e., the selectable marker genes, are expressed less vigorously than the gene of interest which is under the control of the promoter element. Again, cells which are selected based on expression of the selectable marker gene will inherently be higher expressors of the polypeptide of interest.

Accordingly, in one embodiment, the invention is directed to a method of expressing a recombinant polypeptide comprising:

(a) providing as separate elements (i) a first nucleic acid element which comprises a promoter, (ii) a second nucleic acid element which comprises at least one selectable marker gene conferring a selectable phenotype on a cell transfected therewith, an internal ribosome entry site (IRES) sequence positioned upstream of the selectable marker gene, and a transcription termination sequence positioned downstream of the selectable marker gene, and (iii) a third nucleic acid element which comprises a gene encoding said polypeptide;

(b) cotransfecting a population of mammalian cells with each of said first, second and third elements;

(c) culturing said population of cells under conditions whereby the polypeptide and the at least one selectable marker are expressed;

(d) selecting cells which express the selectable marker; and (e) identifying those cells from the selected cells that express the recombinant polypeptide.

In particularly preferred embodiments, the selectable marker gene is selected from the group consisting of a $neo^r$ gene and a dhfr gene and the IRES sequence is derived from an encephalomyocarditis virus (EMCV).

In still a further embodiment, the invention is directed to a selectable marker nucleic acid element comprising: (a) a $neo^r$ gene, (b) a dhfr gene positioned upstream of the $neo^r$ gene, wherein the stop codon for the dhfr gene is replaced with a spacer of about 3 to about 150 nucleotides, such that transcription and translation of both the dhfr and $neo^r$ genes occurs, (c) an internal ribosome entry site (IRES) sequence positioned upstream of the dhfr gene, (d) and a transcription termination sequence positioned downstream of the $neo^r$ gene.

In another embodiment, the invention is directed to a selectable marker nucleic acid element comprising: (a) a $neo^r$ gene which confers reduced resistance to geneticin on a cell transfected therewith as compared to the wild-type $neo^r$ gene, (b) a dhfr gene positioned upstream of the $neo^r$ gene, wherein the stop codon for the dhfr gene is replaced with a spacer of about 12 to about 18 nucleotides, such that transcription and translation of both the dhfr and $neo^r$ genes occurs, (c) an encephalomyocarditis virus internal ribosome entry site (IRES) sequence positioned upstream of the dhfr gene, (d) and a bovine growth hormone transcription termination sequence positioned downstream of the $neo^r$ gene.

In yet further embodiments, the subject invention is directed to mammalian host cells transfected with the above selectable marker nucleic acid elements.

These and other embodiments of the present invention will readily occur to those of ordinary skill in the art in view of the disclosure herein.

DETAILED DESCRIPTION OF THE INVENTION

Figure 1:
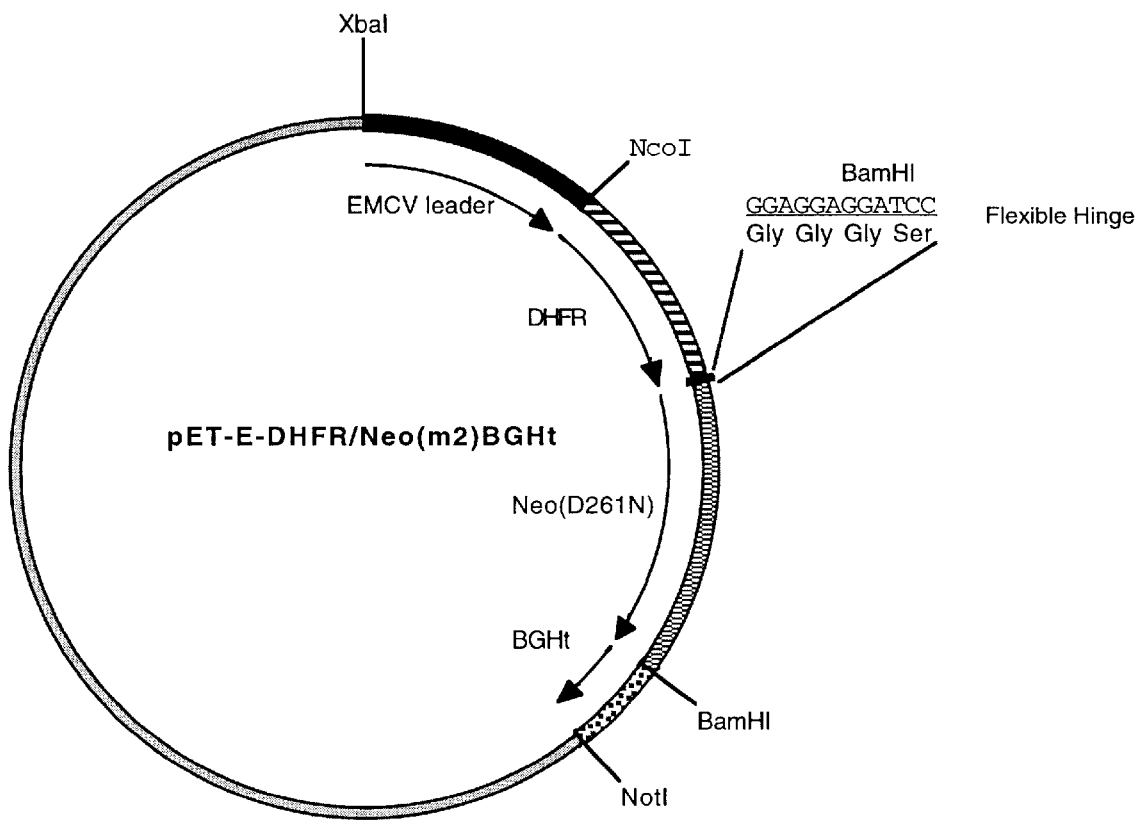
FIG. 1 depicts plasmids pCMVII and pET-E-DHFR/Neo$_{(m2)}$BGHt, used as sources of the CMV promoter element and selectable marker elements, respectively, as described in the examples. The flexible hinge sequence of pET-E-DHFR/Neo(m2)BGHt (SEQ ID NOS:15 & 16) and spacer-containing sequence of pCMVII (SEQ ID NO:17) are shown.
Figure 1:
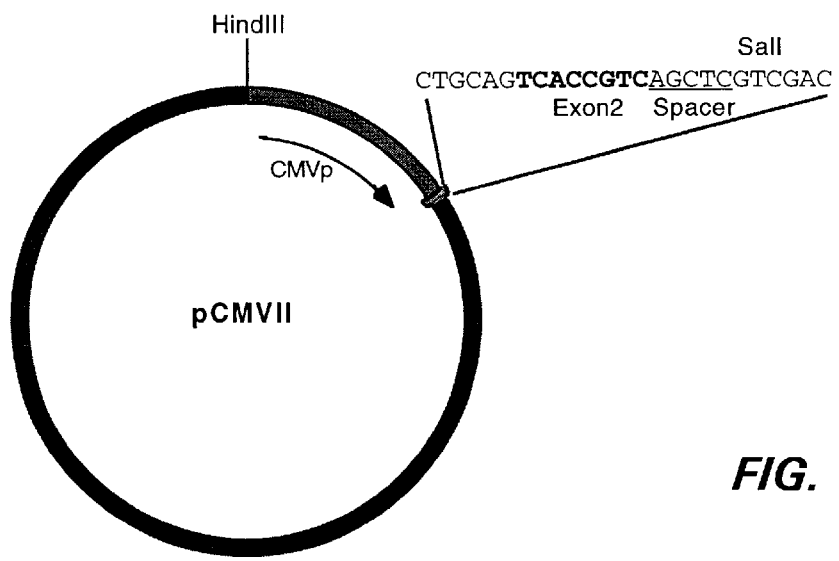

The practice of the present invention will employ, unless otherwise indicated, conventional methods of virology, microbiology, molecular biology, recombinant DNA techniques and immunology within the skill of the art. Such techniques are explained fully in the literature. See, e.g., Sambrook, et al., *Molecular Cloning: A Laboratory Manual* (2nd Edition, 1989); *DNA Cloning: A Practical Approach,* vol. I & II (D. Glover, ed.); *Oligonucleotide Synthesis* (N. Gait, ed., 1984); *A Practical Guide to Molecular Cloning* (1984); *Fundamental Virology,* 2nd Edition, vol. I & II (B. N. Fields and D. M. Knipe, eds.); and *Methods In Enzymology* (S. Colowick and N. Kaplan, eds., Academic Press, Inc.).

As used in this specification and the appended claims, the singular forms "a," "an" and "the" include plural references unless the content clearly dictates otherwise.

I. Definitions

In describing the present invention, the following terms will be employed, and are intended to be defined as indicated below.

The terms "polypeptide" and "protein" refer to a polymer of amino acid residues and are not limited to a minimum length of the product. Thus, peptides, oligopeptides, dimers, multimers, and the like, are included within the definition. Both full-length proteins and fragments thereof are encompassed by the definition. The terms also include postexpression modifications of the polypeptide, for example, glycosylation, acetylation, phosphorylation and the like.

For purposes of the present invention, the polypeptide expressed by the gene of interest may be one useful in a vaccine, therapeutic or diagnostic and may be derived from any of several known viruses, bacteria, parasites and fungi, as well as any of the various tumor antigens. Alternatively, the expressed polypeptide may be a therapeutic hormone, a transcription or translation mediator, an enzyme, an intermediate in a metabolic pathway, an immunomodulator, and the like.

Furthermore, for purposes of the present invention, a "polypeptide" refers to a protein which includes modifications, such as deletions, additions and substitutions (generally conservative in nature), to the native sequence, so long as the protein maintains the desired activity. These modifications may be deliberate, as through site-directed mutagenesis, or may be accidental, such as through mutations of hosts which produce the proteins or errors due to PCR amplification.

A "coding sequence" or a sequence which "encodes" a selected polypeptide, is a nucleic acid molecule which is transcribed (in the case of DNA) and translated (in the case of mRNA) into a polypeptide in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, cDNA from viral, procaryotic or eucaryotic mRNA, genomic DNA sequences from viral (e.g. DNA viruses and retroviruses) or procaryotic DNA, and especially synthetic DNA sequences. A transcription termination sequence may be located 3' to the coding sequence.

A "nucleic acid" molecule can include both double- and single-stranded sequences and refers to, but is not limited to, cDNA from viral, procaryotic or eucaryotic mRNA, genomic DNA sequences from viral (e.g. DNA viruses and retroviruses) or procaryotic DNA, and especially synthetic DNA sequences. The term also captures sequences that include any of the known base analogs of DNA and RNA.

"Operably linked" refers to an arrangement of elements wherein the components so described are configured so as to perform their desired function. Thus, a given promoter operably linked to a coding sequence is capable of effecting the expression of the coding sequence when the proper transcription factors, etc., are present. The promoter need not be contiguous with the coding sequence, so long as it functions to direct the expression thereof. Thus, for example, intervening untranslated yet transcribed sequences can be present between the promoter sequence and the coding sequence, as can translated introns, and the promoter sequence can still be considered "operably linked" to the coding sequence.

"Recombinant" as used herein to describe a nucleic acid molecule means a polynucleotide of genomic, cDNA, viral, semisynthetic, or synthetic origin which, by virtue of its origin or manipulation is not associated with all or a portion of the polynucleotide with which it is associated in nature. The term "recombinant" as used with respect to a protein or polypeptide means a polypeptide produced by expression of a recombinant polynucleotide.

A "control element" refers to a polynucleotide sequence which aids in the expression of a coding sequence to which it is linked. The term includes promoters, transcription termination sequences, upstream regulatory domains, polyadenylation signals, and when appropriate, leader sequences and enhancers, which collectively provide for the transcription and translation of a coding sequence in a host cell.

A "promoter" as used herein is a DNA regulatory region capable of binding RNA polymerase in a mammalian cell and initiating transcription of a downstream (3' direction) coding sequence operably linked thereto. For purposes of the present invention, a promoter sequence includes the minimum number of bases or elements necessary to initiate transcription of a gene of interest at levels detectable above background. Within the promoter sequence is a transcription initiation site, as well as protein binding domains (consensus sequences) responsible for the binding of RNA polymerase. Eucaryotic promoters will often, but not always, contain "TATA" boxes and "CAT" boxes.

By "selectable marker" is meant a gene which confers a phenotype on a cell expressing the marker, such that the cell can be identified under appropriate conditions. Generally, a selectable marker allows selection of transected cells based on their ability to thrive in the presence or absence of a chemical or other agent that inhibits an essential cell function. Suitable markers, therefore, include genes coding for proteins which confer drug resistance or sensitivity thereto, impart color to, or change the antigenic characteristics of those cells transfected with a nucleic acid element containing the selectable marker when the cells are grown in an appropriate selective medium. For example, selectable markers include: cytotoxic markers and drug resistance markers, whereby cells are selected by their ability to grow on media containing one or more of the cytotoxins or drugs; auxotrophic markers by which cells are selected by their ability to grow on defined media with or without particular nutrients or supplements, such as thymidine and hypoxanthine; metabolic markers by which cells are selected for, e.g., their ability to grow on defined media containing the appropriate sugar as the sole carbon source, or markers which confer the ability of cells to form colored colonies on chromogenic substrates or cause cells to fluoresce. Representative selectable markers are described in more detail below.

"Transformation," as used herein, refers to the insertion of an exogenous polynucleotide into a host cell, irrespective of the method used for insertion: for example, transformation by direct uptake, transfection, infection, and the like. For particular methods of transfection, see further below. The exogenous polynucleotide may be maintained as a nonintegrated vector, for example, an episome, or alternatively, may be integrated into the host genome.

By "cotransfection" is meant the simultaneous or substantially simultaneous delivery of more than one nucleic acid element to the same host cell or population of cells, regardless of the method used. Thus, the various nucleic acid elements of the present invention may be delivered simultaneously by combining all elements in the transfection reaction or by sequentially delivering the various elements, in any order, to the host cell or population of cells.

"Homology" refers to the percent identity between two polynucleotide or two polypeptide moieties. Two DNA, or two polypeptide sequences are "substantially homologous" to each other when the sequences exhibit at least about 75%–85%, preferably at least about 90%, and most preferably at least about 95%–98% sequence identity over a defined length of the molecules. As used herein, substantially homologous also refers to sequences showing complete identity to the specified DNA or polypeptide sequence.

Percent "identity" between two amino acid or polynucleotide sequences can be determined by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN, Dayhoff, M. O. in *Atlas of Protein Sequence and Structure* M. O. Dayhoff ed., 5 Suppl. 3:353–358, National biomedical Research Foundation, Washington, D.C., which adapts the local homology algorithm of Smith and Waterman (1981) *Advances in Appl. Math.* 2:482–489 for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Alternatively, identity can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning*, supra; *Nucleic Acid Hybridization*, supra.

II. Modes of Carrying Out the Invention

The present invention is based on the development of a novel noncloning method for recombinantly producing a desired protein. In particular, the invention utilizes three basic elements: (1) a promoter element; (2) at least one gene of interest; and (3) a selectable marker cassette which includes in 5' to 3' order, an internal ribosome entry site ("IRES"), at least one gene coding for a selectable marker, a transcription termination sequence and, optionally, a polyadenylation signal. The three basic elements are cotransfected into a mammalian host cell where they become operably linked such that expression of the gene of interest and the selectable marker gene occur.

In order to facilitate appropriately ordered ligation of the various fragments in the host cell, the DNA fragment bearing the gene of interest may be treated with appropriate enzymes such that cohesive termini complimentary to the 3' and 5' termini of the promoter and selection cassette fragments, respectively are produced. In this way, ordered association of the fragments may occur in vivo.

The noncloning technique of the present invention eliminates the need to subclone the gene of interest and can be used in a wide variety of contexts, such as to express PCR products encoding both known and unknown proteins, as well as for the expression of synthetic nucleic acid sequences, cDNA libraries, genomic DNA derived directly from a virus or organism of interest, and the like.

Furthermore, particular embodiments of the present invention take advantage of selectable marker nucleic acid elements designed to select cells which are high protein expressors. For example, attenuated drug resistance genes can be used in the selectable marker elements which require greater amounts of the selectable marker to be expressed in order to overcome the weaker resistance conferred by the gene. Hence, cells selected based on expression of the marker will inherently contain higher levels of the recombinant product.

Additionally, the selectable marker elements are designed with an IRES sequence such that the downstream selectable marker genes are expressed less vigorously than the gene of interest which is under the control of the promoter element. Thus, cells which are selected based on expression of the selectable marker gene will inherently be high expressors of the polypeptide of interest. Finally, more than one marker gene and/or amplifiers may be used in the selectable marker construct to assure enhanced expression of the selectable marker gene.

Thus, the methods of the present invention will find use for the expression of a wide variety of substances, including peptides which act as antibiotics and antiviral agents, e.g., immunogenic peptides for use in vaccines and diagnostics; antineoplastics; immunomodulators, such as any of the various cytokines including interleukin-1, interleukin-2, interleukin-3, interleukin-4, and gamma-interferon; peptide hormones such as insulin, proinsulin, growth hormone, GHRH, LHRH, EGF, somatostatin, SNX-111, BNP, insulinotropin, ANP, FSH, LH, PSH and hCG, gonadal steroid hormones (androgens, estrogens and progesterone), thyroid-stimulating hormone, inhibin, cholecystokinin, ACTH, CRF, dynorphins, endorphins, endothelin, fibronectin fragments, galanin, gastrin, insulinotropin, glucagon, GTP-binding protein fragments, guanylin, the leukokinins, magainin, mastoparans, dermaseptin, systemin, neuromedins, neurotensin, pancreastatin, pancreatic polypeptide, substance P, secretin, thymosin, and the like; and growth factors, such as PDGF, EGF, KGF, IGF-1 and IGF-2, FGF, and the like.

More particularly, proteins for use in vaccines and diagnostics may be of viral, bacterial, fungal or parasitic origin, including but not limited to, those encoded by human and animal viruses and can correspond to either structural or non-structural proteins. For example, the present system will find use for recombinantly producing a wide variety of proteins from the herpesvirus family, including proteins derived from herpes simplex virus (HSV) types 1 and 2, such as HSV-1 and HSV-2 glycoproteins gB, gD and gH; proteins derived from varicella zoster virus (VZV), Epstein-Barr virus (EBV) and cytomegalovirus (CMV) including CMV gB and gH; and proteins derived from other human herpesviruses such as HHV6 and HHV7. (See, e.g. Chee et al., *Cytomegaloviruses* (J. K. McDougall, ed., Springer-Verlag 1990) pp. 125–169, for a review of the protein coding content of cytomegalovirus; McGeoch et al., *J. Gen. Virol.* (1988) 69:1531–1574, for a discussion of the various HSV-1 encoded proteins; U.S. Pat. No. 5,171,568 for a discussion of HSV-1 and HSV-2 gB and gD proteins and the genes encoding therefor; Baer et al., *Nature* (1984) 310:207–211, for the identification of protein coding sequences in an EBV genome; and Davison and Scott, *J. Gen. Virol.* (1986) 67:1759–1816, for a review of VZV.)

Polynucleotide sequences encoding proteins from the hepatitis family of viruses, including hepatitis A virus (HAV), hepatitis B virus (HBV), hepatitis C virus (HCV), the delta hepatitis virus (HDV), hepatitis E virus (HEV) and hepatitis G virus (HGV), can also be conveniently used in the techniques described herein. By way of example, the viral genomic sequence of HCV is known, as are methods for obtaining the sequence. See, e.g., International Publication Nos. WO 89/04669; WO 90/11089; and WO 90/14436. The HCV genome encodes several viral proteins, including E1 (also known as E) and E2 (also known as E2/NSI). (See, Houghton et al., *Hepatology* (1991) 14:381–388, for a discussion of HCV proteins, including E1 and E2.) The sequences encoding each of these proteins, as well as antigenic fragments thereof, will find use in the present methods. Similarly, the coding sequence for the δ-antigen from HDV is known (see, e.g., U.S. Pat. No. 5,378,814) and this sequence can also be conveniently used in the present methods. Additionally, antigens derived from HBV, such as the core antigen, the surface antigen, sAg, as well as the presurface sequences, preS1 and preS2 (formerly called preS), as well as combinations of the above, such as sAg/preS1, sAg/preS2, sAg/preS1/preS2, and preS1/preS2, will find use herein. See, e.g., "HBV Vaccines—from the laboratory to license: a case study" in Mackett, M. and Williamson, J. D., *Human Vaccines and Vaccination*, pp.

159–176, for a discussion of HBV structure; and U.S. Pat. Nos. 4,722,840, 5,098,704, 5,324,513, incorporated herein by reference in their entireties; Beames et al., *J. Virol.* (1995) 69:6833–6838, , Birnbaum et al., *J. Virol.* (1990) 64:3319–3330; and Zhou et al., *J. Virol.* (1991) 65:5457–5464.

Polynucleotide sequences encoding proteins derived from other viruses will also find use in the claimed methods, such as without limitation, proteins from members of the families Picornaviridae (e.g., polioviruses, etc.); Caliciviridae; Togaviridae (e.g., rubella virus, dengue virus, etc.); Flaviviridae; Coronaviridae; Reoviridae; Birnaviridae; Rhabodoviridae (e.g., rabies virus, etc.); Filoviridae; Paramyxoviridae (e.g., mumps virus, measles virus, respiratory syncytial virus, etc.); Orthomyxoviridae (e.g., influenza virus types A, B and C, etc.); Bunyaviridae; Arenaviridae; Retroviradae (e.g., HTLV-I; HTLV-II; HIV-1 (also known as HTLV-III, LAV, ARV, hTLR, etc.)), including but not limited to antigens from the isolates $HIV_{IIIb}$, $HIV_{SF2}$, $HIV_{LAV}$, $HIV_{LAI}$, $HIV_{MN}$); $HIV-1_{CM235}$, $HIV-1_{US4}$; HIV-2; simian immunodeficiency virus (SIV) among others. See, e.g. *Virology*, 3rd Edition (W. K. Joklik ed. 1988); *Fundamental Virology*, 2nd Edition (B. N. Fields and D. M. Knipe, eds. 1991), for a description of these and other viruses.

For example, the invention may be used to express genes encoding the gp120 envelope protein from any of the above HIV isolates. The gp120 sequences for a multitude of HIV-1 and HIV-2 isolates, including members of the various genetic subtypes of HIV, are known and reported (see, e.g., Myers et al., Los Alamos Database, Los Alamos National Laboratory, Los Alamos, N. Mex. (1992); Myers et al., *Human Retroviruses and Aids*, 1990, Los Alamos, N. Mex.: Los Alamos National Laboratory; and Modrow et al., *J. Virol.* (1987) 61:570–578, for a comparison of the envelope gene sequences of a variety of HIV isolates) and sequences derived from any of these isolates will find use in the present methods. Furthermore, the invention is equally applicable to other immunogenic proteins derived from any of the various HIV isolates, including any of the various envelope proteins such as gp160 and gp41, gag antigens such as p24gag and p55gag, as well as proteins derived from the pol region.

The present invention will also find use for the expression of influenza virus proteins. Specifically, the envelope glycoproteins HA and NA of influenza A are of particular interest for generating an immune response. Numerous HA subtypes of influenza A have been identified (Kawaoka et al., *Virology* (1990) 179:759–767; Webster et al., "Antigenic variation among type A influenza viruses," p. 127–168. In: P. Palese and D. W. Kingsbury (ed.), *Genetics of influenza viruses*. Springer-Verlag, New York). Thus, the gene sequences encoding proteins derived from any of these isolates can also be used in the recombinant production techniques described herein.

Furthermore, the methods described herein provide a means for producing proteins useful for treating a variety of malignant cancers. For example, the system of the present invention can be used to produce a variety of tumor antigens which in turn may be used to mount both humoral and cell-mediated immune responses to particular proteins specific to the cancer in question, such as an activated oncogene, a fetal antigen, or an activation marker. Such tumor antigens include any of the various MAGEs (melanoma associated antigen E), including MAGE 1, 2, 3, 4, etc. (Boon, T. *Scientific American* (March 1993):82–89); any of the various tyrosinases; MART 1 (melanoma antigen recognized by T cells), mutant ras; mutant p53; p97 melanoma antigen; CEA (carcinoembryonic antigen), among others.

It is readily apparent that the subject invention can be used to produce a variety of proteins useful for the prevention, treatment and/or diagnosis of a wide variety of diseases.

Polynucleotide sequences coding for the above-described molecules can be obtained using recombinant methods, such as by screening cDNA and genomic libraries from cells expressing the gene, or by deriving the gene from a vector known to include the same. Furthermore, the desired gene can be isolated directly from cells and tissues containing the same, using standard techniques, such as phenol extraction and PCR of cDNA or genomic DNA. See, e.g., Sambrook et al., supra, for a description of techniques used to obtain and isolate DNA. The gene of interest can also be produced synthetically, rather than cloned. The nucleotide sequence can be designed with the appropriate codons for the particular amino acid sequence desired. In general, one will select preferred codons for the intended host in which the sequence will be expressed. The complete sequence is assembled from overlapping oligonucleotides prepared by standard methods and assembled into a complete coding sequence. See, e.g., Edge, *Nature* (1981) 292:756; Nambair et al., *Science* (1984) 223:1299; Jay et al., *J. Biol. Chem.* (1984) 259:6311.

The promoter for use in the present invention is one which will direct transcription of the gene of interest, as well as the selectable marker, in a mammalian host cell when operably linked thereto. Typical promoters for mammalian cell expression include the SV40 early promoter, a CMV promoter such as the CMV immediate early promoter, the mouse mammary tumor virus LTR promoter, the adenovirus major late promoter (Ad MLP), and the herpes simplex virus promoter, among others. Other nonviral promoters, such as a promoter derived from the murine metallothionein gene, will also find use for mammalian expression. These and other promoters can be obtained from commercially available plasmids, using techniques well known in the art. See, e.g., Sambrook et al., supra. Enhancer elements may used in association with the promoter to increase expression levels of the mammalian constructs. Examples include the SV40 early gene enhancer, as described in Dijkema et al., *EMBO J.* (1985) 4:761, the enhancer/promoter derived from the long terminal repeat (LTR) of the Rous Sarcoma Virus, as described in Gorman et al., *Proc. Natl. Acad. Sci. USA* (1982b) 79:6777 and elements derived from human CMV, as described in Boshart et al., *Cell* (1985) 41:521, such as elements included in the CMV intron A sequence.

A particularly preferred promoter for use with the present invention is the human cytomegalovirus immediate-early enhancer/promoter, known as HCMV IE1, which includes the CMV intron A. See, e.g., Chapman et al., *Nuc. Acids Res.* (1991) 19:3979–3986; Boshart et al., *Cell* (1985) 41:521. This promoter is found in, e.g., plasmid pCMV6. See, e.g., Chapman et al., supra; and U.S. Pat. No. 5,688,688, incorporated herein by reference in its entirety.

As explained above, the system of the invention also includes an element encoding one or more selectable markers. A number of suitable selectable markers can be used in the practice of the invention, such as a marker which imparts resistance to a cytotoxic agent to the transformed mammalian cell. The cytotoxic agent can be, but is not limited to, neomycin and neomycin analogues such as geneticin, hygromycin, and the like. For example, the gene encoding aminoglycoside-phosphotranferase (APH) allows selection in mammalian cells by conferring resistance to neomycin. Several mutations to this gene have been described which impart resistance to the neomycin analogue geneticin (G418) (available from Sigma, St. Louis, Mo.). For example, an APH with aspartic acid at position 261 replaced by an asparagine, confers reduced resistance to gentamicin. See, e.g., Blazquez et al., *Molec. Micro.* (1991) 5:1511–1518. This, or other selectable markers that confer attenuated resistance to toxic agents as compared to their wild-type counterparts are particularly preferred as such genes require larger amounts of protein to be expressed in order to overcome the weaker resistance conferred by the attenuated gene.

Other markers useful herein include cell surface markers such as alkaline phosphatase, nerve growth factor receptor, or any other suitable membrane-associated moiety. Representative examples of such markers and associated prodrug molecules include alkaline phosphatase and various toxic phosphorylated compounds such as phenolmustard phosphate, doxorubicin phosphate, mitomycin phosphate and etoposide phosphate; β-galactosidase and N-[4-(β-D-galactopyranosyl) benyloxycarbonyl]-daunorubicin; azoreductase and azobenzene mustards; β-glucosidase and amygdalin; β-glucuronidase and phenolmustard-glucuronide and epirubicin-glucuronide; carboxypeptidase A and methotrexate-alanine; cytochrome P450 and cyclophosphamide or ifosfamide; DT diaphorase and 5-(aziridine-1-yl)-2,4,dinitrobenzamide (CB1954) (Cobb et al. (1969) *Biochem. Pharmacol* 18:1519, Knox et al. (1993) *Cancer Metastasis Rev.* 12:195); β-glutamyl transferase and β-glutamyl p-phenylenediamine mustard; nitroreductase and CB1954 or derivatives of 4-nitrobenzyloxycarbonyl; glucose oxidase and glucose; xanthine oxidase and hypoxanthine; and plasmin and peptidyl-p-phenylenediamine-mustard. Nonimmunogenic markers may also be made by expressing an enzyme in a compartment of the cell where it is not normally expressed.

Still other suitable markers are genes which impart color to those cells transfected with a nucleic acid element containing the selectable marker such that detection can be achieved by virtue of a color change (either visible or fluorescent). For example, the gene encoding Green Fluorescent Protein (GFP) may be used as the selectable marker, as can derivatives thereof such as Enhanced Green Fluorescent Protein (EGFP), and like molecules.

These and other selectable markers can be obtained from commercially available plasmids, using techniques well known in the art. See, e.g., Sambrook et al., supra.

Expression can also be amplified by placing an amplifiable gene, such as the mouse dihydrofolate reductase (dhfr) gene adjacent to the coding sequence. Cells can then be selected for methotrexate resistance in dhfr-deficient cells. See, e.g. Urlaub et al. (1980) *Proc. Natl. Acad. Sci. USA* 77:4216–4220; Ringold et al. (1981) *J. Mol. and Appl. Genet.* 1:165–175.

Transcription termination and polyadenylation sequences may also be present on the selectable marker element, located 3' to the translation stop codon for the selectable marker. Examples of transcription terminator/polyadenylation signals include, but are not limited to, those derived from SV40, as described in Sambrook et al., supra, as well as a bovine growth hormone terminator sequence. Additionally, 5'-UTR sequences can be placed adjacent to the coding sequence of the selectable marker in order to enhance expression of the same. Particularly useful with the present system are UTRs which include an Internal Ribosome Entry Site (IRES) present in the leader sequences of picornaviruses such as the encephalomyocarditis virus (EMCV) UTR (Jang et al. *J. Virol.* (1989) 63:1651–1660. Other picornavirus UTR sequences that will also find use in the present invention include the polio leader sequence and hepatitis A virus leader and the hepatitis C IRES.

A particular advantage of structuring the system as described above is that those sequences downstream of the IRES elements, i.e., the selectable marker genes, may be expressed less vigorously than the gene of interest which is under the control of the promoter element. Thus, cells which are selected based on expression of the selectable marker gene will inherently be high expressors of the polypeptide of interest.

If more than one selectable marker is present in the element, a spacer region can be incorporated between the two genes in place of the stop codon, in order to assure continuous read-through of the marker genes. Such a spacer will normally include about 3 to about 150 nucleotides, more preferably about 6 to about 60 nucleotides, even more preferably about 6 to about 30 nucleotides, and most preferably about 12 to about 18 nucleotides. The only requirements for the spacer region is that continuous read-through is maintained and that the spacer does not encode a polypeptide sequence that will interfere with the function of the markers or the gene of interest.

Figure 2:
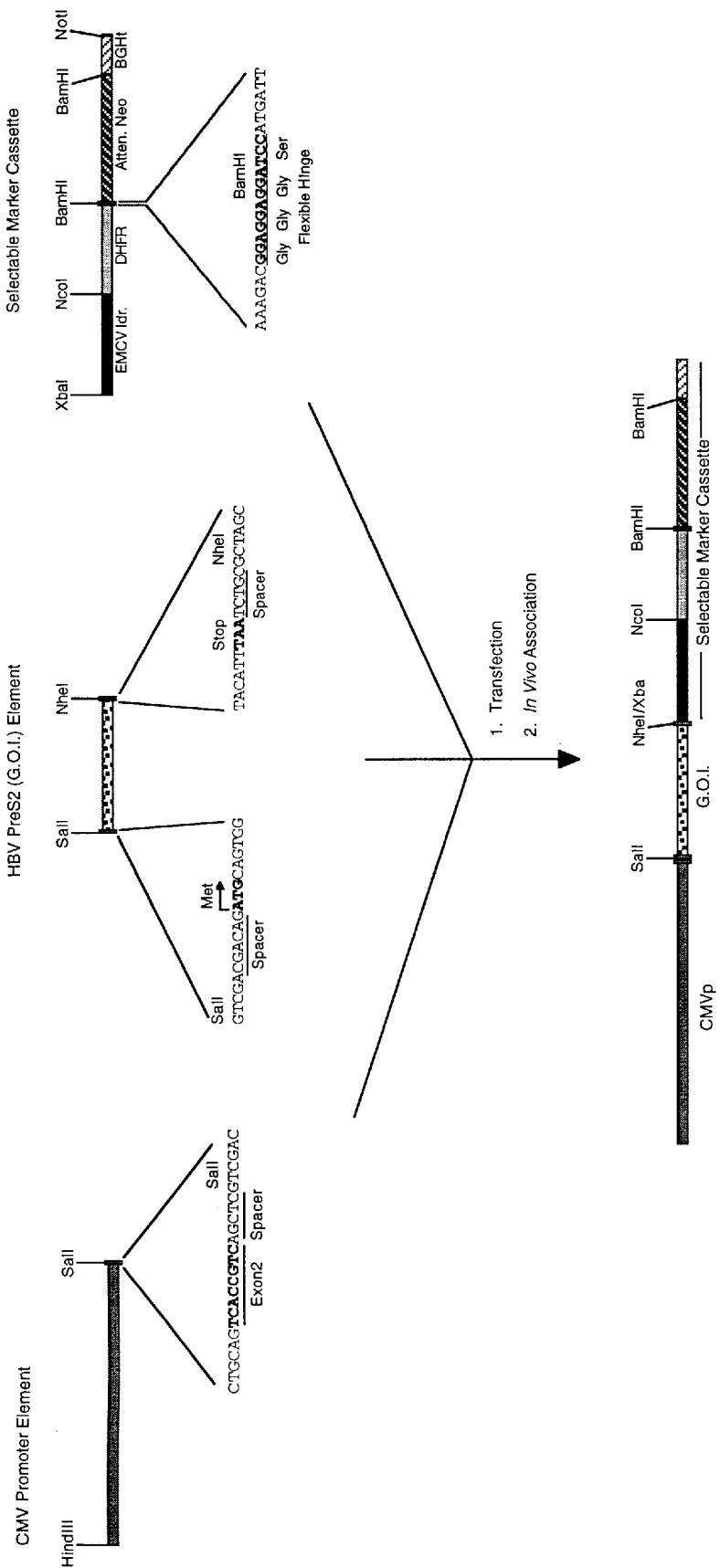
FIG. 2 shows one strategy used to effect expression of a gene of interest in a mammalian host cell using the system of the present invention. A CMV promoter element, selectable marker cassette, as well as a nucleic acid element comprising a gene encoding an hepatitis B virus (HBV) preS2 polypeptide (termed "G.O.I." (gene of interest)) is shown in the figure. The spacer-containing sequences of the CMV promoter element (SEQ ID NO:18), G.O.I. element (SEQ ID NOS:17 & 18) and the flexible hinge-containing sequence of the selectable marker cassette (SEQ ID NO:19) are shown.

A particularly preferred selectable marker element for use with the present invention includes a wildtype dhfr gene fused to an attenuated form of the gene conferring reduced neomycin resistance (termed neo$^r$). See, e.g., Blazquez et al., *Molec. Micro.* (1991) 5:1511–1518 for a description of the mutated neo$^r$ gene. The attenuated gene encodes an aminoglycoside-phosphotransferase with the aspartic acid at position 261 replaced by an asparagine. This element provides selection based on the ability of the transfected cell to grow on geneticin-supplemented media, as well as amplification using the dhfr gene and selection based on methotrexate resistance. The element includes a spacer of 12 nucleotides that encodes the amino acid sequence Gly-Gly-Gly-Ser located between the dhfr and attenuated neo$^r$ genes, in place of the translation stop codon for the dhfr gene. The element also includes the EMCV IRES sequence located upstream of the dhfr and neo genes. Finally, a bovine growth hormone transcription termination sequence is located 3' to the translation stop codon for the neo sequence. This element is shown in FIGS. 1 and 2.

Prior to transfection, appropriate enzymes are used to create overlapping untranslated sequences between the gene of interest, promoter and selectable marker elements, to assure complimentarity between the three elements so that an ordered ligation of these elements occurs in the host cell. Such enzymes include restriction enzymes, exonucleases and polymerases, such as T4 polymerase, all of which are well known in the art. For example, restriction endonucleases with various specificities have been isolated from a wide range of prokaryotes and are well known in the art. See, e.g., Sambrook et al., supra. The choice of an appropriate restriction endonuclease depends on the particular sequence targeted. One of skill in the art will readily recognize the proper restriction enzyme to use for a desired sequence. Generally, the overlapping sequences will include about 3 to about 150 nucleotides, more preferably about 4 to about 50 nucleotides, and most preferably about 4 to about 10 nucleotides. Alternatively, blunt-end ligations can occur in vivo such that overlapping sequences are not necessary.

Furthermore, each of the fragments may include untranslated spacer residues, at the 5' and 3' ends, to protect the fragment from exonucleolytic activity in transfected cells. Such extensions will generally be about 3 to as many as 1000 nucleotides in length, more typically 3–50 nucleotides in length, and preferably 5–25 nucleotides in length.

Once the various elements are constructed, they are used to transfect eucaryotic cells, such as mammalian, insect or yeast cells. Mammalian cells for use as hosts with the present invention include many primary and immortalized cell lines, available from the American Type Culture Collection (ATCC), including but not limited to, Chinese hamster ovary (CHO) cells, HeLa cells, baby hamster kidney (BHK) cells, monkey kidney cells (COS), human hepatocellular carcinoma cells (e.g., Hep G2), and a number of other cell lines. Yeast hosts include *Saccharomyces cerevisiae Saccharomyces carlsbergeneis, Candida albicans, Candida maltosa, Hansenula polymorpha, Kluyveromyces fragilis, Kluyveromyces lactis, Pichia guillerimondii, Pichia pastoris* and *Schizosaccharomyces pombe.* Insect systems include for example recombinant baculovirus expression vectors for infection of inter alia, *Aedes aegypti, Autographa californica, Bombyx mori, Drosophila melanogaster, Spodoptera frugiperda,* and *Trichoplusia ni.*

A wide variety of methods can be used to deliver the gene of interest, promoter and selectable marker elements to mammalian cells. Such methods include DEAE dextran-mediated transfection, calcium phosphate precipitation, polylysine- or polyornithine-mediated transfection, or precipitation using other insoluble inorganic salts, such as strontium phosphate, aluminum silicates including bentonite and kaolin, chromic oxide, magnesium silicate, talc, and the like. Other useful methods of transfection include electroporation, sonoporation, protoplast fusion, liposomes, peptoid delivery, or microinjection. See, e.g., Sambrook et al., supra, for a discussion of techniques for transfecting mammalian cells.

For example, the elements can be packaged in liposomes prior to delivery to the cells. Lipid encapsulation is generally accomplished using liposomes which are able to stably bind or entrap and retain nucleic acid. The ratio of condensed DNA to lipid preparation can vary but will generally be around 1:1 (mg DNA:micromoles lipid), or more of lipid. For a review of the use of liposomes as carriers for delivery of nucleic acids, see, Hug and Sleight, *Biochim. Biophys. Acta.* (1991) 1097:1–17; Straubinger et al., in *Methods of Enzymology* (1983), Vol. 101, pp. 512–527.

Liposomal preparations for use with the present invention include cationic (positively charged), anionic (negatively charged) and neutral preparations, with cationic liposomes particularly preferred. Cationic liposomes are readily available. For example, N[1-2,3-dioleyloxy)propyl]-N,N,N-triethylammonium (DOTMA) liposomes are available under the trademark LIPOFECTIN™, from GIBCO BRL, Grand Island, N.Y. (See, also, Felgner et al., *Proc. Natl. Acad. Sci. USA* (1987) 84:7413–7416). Other commercially available lipids include transfectace (DDAB/DOPE) and DOTAP/DOPE (Boerhinger). Other cationic liposomes can be prepared from readily available materials using techniques well known in the art. See, e.g., Szoka et al., *Proc. Natl. Acad. Sci. USA* (1978) 75:4194–4198; PCT Publication No. WO 90/11092 for a description of the synthesis of DOTAP (1,2-bis(oleoyloxy)-3-(trimethylammonio)propane) liposomes. The various liposome-nucleic acid complexes are prepared using methods known in the art. See, e.g., Straubinger et al., in METHODS OF IMMUNOLOGY (1983), Vol. 101, pp. 512–527; Szoka et al., *Proc. Natl. Acad. Sci. USA* (1978) 75:4194–4198; Papahadjopoulos et al., *Biochim. Biophys. Acta* (1975) 394:483; Wilson et al., *Cell* (1979) 17:77); Deamer and Bangham, *Biochim. Biophys. Acta* (1976) 443:629; Ostro et al., *Biochem. Biophys. Res. Commun.* (1977) 76:836; Fraley et al., *Proc. Natl. Acad. Sci. USA* (1979) 76:3348); Enoch and Strittmatter, *Proc. Natl. Acad. Sci. USA* (1979) 76:145); Fraley et al., *J. Biol. Chem.* (1980) 255:10431; Szoka and Papahadjopoulos, *Proc. Natl. Acad. Sci. USA* (1978) 75:145; and Schaefer-Ridder et al., *Science* (1982) 215:166.

The DNA can also be delivered in cochleate lipid compositions similar to those described by Papahadjopoulos et al., *Biochem. Biophys. Acta.* (1975) 394:483–491. See, also, U.S. Pat. Nos. 4,663,161 and 4,871,488.

After transfection, cells which express the gene of interest are selected away from those that do not, based on expression of the selectable marker. For example, if the selectable marker element used confers resistance to a cytotoxic agent, the cells can be contacted with the appropriate cytotoxic agent, whereby nontransfected cells, as well as nonexpressing or very low expressing cells, are negatively selected away from the transfected cells. If the selectable marker is a cell surface marker, the cells can be contacted with a binding agent specific for the particular cell surface marker, whereby the transfected cells can be positively selected away from the population.

The selection step can also entail fluorescence-activated cell sorting (FACS) techniques, such as where FACS is used to select cells from the population containing a particular surface marker. These cell sorting procedures are described in detail, for example, in the FACSVantage™ Training Manual, with particular reference to sections 3-11 to 3-28 and 10-1 to 10-17. The selection step may also use magnetically responsive particles as retrievable supports for target cell capture and/or background removal. These and similar separation procedures are described, for example, in the Baxter Immunotherapy Isolex training manual.

Various modifications of the above-described system can be made in order to enhance ligation of the various fragments in the host cell. For example, cell lines expressing a ligase in the cytoplasm, such as bacteriophage T4 DNA ligase, can be used in the methods of the invention. This ligase acts to join complementary, cohesive DNA termini and may be used to aid in linking the various elements in an orderly fashion. *E. coli* DNA ligase can also be used with the method of the invention.

Additionally, techniques can be used to aid in selection of clones containing the properly ligated construct. For example, a toxin cassette, driven by a second IRES sequence, can be incorporated into the selectable marker element, upstream of the IRES sequence which is associated with the selectable marker gene. A splice acceptor sequence is then located at the junction of the first transcription terminator and the IRES sequence adjacent the selectable marker gene. The gene of interest is then designed to include a splice donor at its 3' end. Accordingly, correct ligation between the gene of interest and the selectable marker element ensures removal of the toxin gene. Independent integration of the selectable marker element bearing the toxin gene will lead to cell death and hence, no clones.

Alternatively, GFP or its derivatives, such as but not limited to EGFP, may replace the drug resistance gene in the selectable marker cassette, permitting FACS cell sorting of highly expressing clones, as described above.

Once expressed, the product may be isolated and purified by any number of techniques, well known in the art, including: chromatography, e.g., HPLC, affinity chromatography, ion exchange chromatography, size-exclusion, etc.; electrophoresis; density gradient centrifugation; solvent extraction, or the like. See, e.g., *Protein Purification Principles and Practice,* 2nd edition (Robert K. Scopes ed. 1987); and *Protein Purification Methods, a Practical Approach* (E. L. V. Harris and S. Angal, eds. 1990).

III. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

EXAMPLE 1

Recombinant Production of HBV preS2

Materials and Methods

Cell Culture: dhfr-negative CHOdg44 (Urlaub et al., (1980) *Proc. Natl. Acad. Sci. USA* 77:4216–4220) cells were grown in Ham's nutrient F12 medium (JRH, Inc. Lenexa, Kans.) supplemented with penicillin (2 nM), streptomycin (100 µg/ml), glutamine (2 nM), proline (2 µg/ml), and non-essential amino acids (Gibco). DNA fragments were introduced into the cells by LT1 (Pan Vera Corp. Madison, Wis.) transfection. Briefly, 2 µg of each DNA fragment to be transfected were mixed (unligated) prior to addition of 30 µg of the LT1 reagent. This mixture was applied to twice washed monolayers in serum-free OPTIMEM (Gibco) and cells incubated 4 h, 37° C. Monolayers were washed once, overlayed with growth medium for 48 h, then subcultured 1:10 into selective medium. The dhfr selective medium consisted of Ham's F12 medium lacking hypoxanthine, thymidine, and glycine that was supplemented as for the nutrient F12 medium except for the use of 10% dialyzed fetal calf serum; for dual dhfr/neo$^r$ selection, dhfr selective medium was supplemented with 250 µg/ml geneticin (Gibco). After approximately 15–21 days individual colonies were isolated to individual wells of a 96 well plate and expanded in selective media lacking geneticin. When clones reached confluence in the 96 well plate, they were transferred to an individual well of a 24 well plate and further expanded. At confluence or at near confluence in the 24 well plate, individual clones were tested for HBV surface antigen (sAg) expression. Positive clones were transferred to $T_{25}$ (or 25 cm$^2$) culture flasks and were carried for 6–8 passages to assess stability of expression by assaying medium from near confluent monolayer cultures that had been incubated 48 h in fresh culture medium. Stably expressing clones of comparable sAg titer were pooled and subjected to methotrexate (Mtx) amplification in dhfr selective medium at increasing concentrations of drug (10, 20, 50 nM). Individual clones from first round amplification were analyzed as described above; clones of comparable sAg titer were pooled and subjected to a second round of Mtx amplification at increasing concentrations of drug (50, 100, 500, or 1000 nM). Individual clones from this round of amplification were similarly analyzed as described above.

Plasmids and DNA manipulations:

Plasmid pCMVII: The CMV enhancer/promoter plus Intron A was transferred from pCMV6 (Chapman et al., *Nuc. Acids Res.* (1991) 19:3979–3986) as a HindIII-SalI fragment into pUC19 (New England Biolabs, Inc., Beverly, Mass.) together with the bovine growth hormone terminator from pCDNA3 (Invitrogen, Inc., Carlsbad, Calif.) to give pCMVII.

Plasmid pET-EMCV-DHFR/Neo: The EMCV leader was PCR-amplified from pCite-4a+ (Novagen, Inc., Milwaukee, Wis.) and inserted into pET-23d (Novagen, Inc., Milwaukee, Wis.) as an Xba-Nco fragment to give PET-EMCV. The dhfr gene was PCR-amplified using primers 38 and 75, described below, to give a product with a Gly-Gly-Gly-Ser spacer in place of the translation stop codon and inserted as an Nco-BamH1 fragment to give pET-E-DHFR. Next, the attenuated neo gene was PCR amplified from pSV2Neo (Clontech, Palo Alto, Calif.) using primers 91 and 93, described below, and inserted into the unique BamH1 site of pET-E-DHFR to give pET-E-DHFR/Neo$_{(m2)}$. Finally the bovine growth hormone terminator was transferred from pCMVII and inserted downstream of the neo gene to give pET-E-DHFR/Neo$_{(m2)}$BGHt (FIG. 1).

CMV Promoter Element: For preparation of the CMV promoter (CMVp) fragment for cell transfections, pCMVII was cleaved with HindIII and SalI; the EMCV-dhfr/neo selectable marker cassette fragment was prepared by cleavage of pET-E-DHFR/Neo$_{(m2)}$BGHt with Xba1 and Not1. Plasmids were purified using QIAGEN MAXI™ purification kits (Qiagen Corp., Santa Clarita, Calif.)

PCR Primers: The primers for use in obtaining the gene encoding hepatitis B virus (HBV) preS2, were primer 83 (5'-GTCGACGACAGATGCAGTGGAATTCCACT-3') (SEQ ID NO:1) and primer 84 (5'-GCTAGCGCAGATTAAATGTATACCCAGAGACA-3') (SEQ ID NO:2). The mutant neo primers were 91 (5'tcagaagaactcgttaagaa-3') (SEQ ID NO:3) and 93 (5'-TTGAACAAGATGGATT-3') (SEQ ID NO:4). The DHFR primers were 38 (5'-CCATGGTTCGACCATTGGAA-3') (SEQ ID:5) and 75 (5'-GGATCCCCGCCGTCTTTCTTCTCGTA-3') (SEQ ID NO:6). The junction RT-PCR primers for the CMVp-preS2 junction were 126 (5'-GGGAACGGTGCATTGGAA-3') (SEQ ID NO:7) and 127 (5'-CCCTGACTCTGGGATCC-3') (SEQ ID NO:8) or 95 (5'-CCACGCTGTTTTGACCTC-3') (SEQ ID NO:9) and 96 (5'-CCGTACTGGTTGTTGTTGA-3') (SEQ ID NO:10); primers for the preS2-EMCV leader junction were 128 (5'-CGTGAGTCCCTTTATACCG-3') (SEQ ID NO:11) and 129 (5'-CGGCCAGTAACGTTAGGG-3') (SEQ ID NO:12) or 98 (5'-TATAGACAAACGCACACCG-3') (SEQ ID NO:13) and 123 (5'-AACCAGTACGGGACCATG-3') (SEQ ID NO:14).

PCR amplification of preS2: The HBV gene encoding preS2 was prepared by a modified hot-start PCR amplification prior to each transfection using the thermostable proofreading polymerase pfu (Stratagene, La Jolla, Calif.). The source of the template DNA was extracted human donor plasma containing subtype adw HBV (Boston Biomedica, Inc., West Bridgewater, Mass.) Cycling conditions were 95° C. for 3 min., addition of enzyme, followed by 5 cycles of 95° C. for 1 min. 50° C. for 1 min., 72° C. for 2 min., followed by 30 cycles of 95° C. for 1 min., 76° C. for 1 min., 72° C. for 2 min., followed by 1 cycle of 72° C. for 10 min. PCR products were digested with Sal1 and Nhe1 to give compatible termini with those of the CMV promoter and selectable marker fragments.

Immunodetection: Surface antigen titers were determined using the AUZYME™ EIA (Abbott Laboratories, Abbott Park, Ill.) on supernatants from individual clones according to supplier's instructions. For radiolabelling, 8×10$^5$ cells were seeded into 60 mm plates 16 h prior to labelling. Cells were starved for 1 h in serum-free DMEM lacking methionine and cysteine then labelled 3 h with 10 µCi$^{35}$S-REDIVUE PRO-MIX™ (Amersham, Arlington Heights, Ill.) followed by a 16 h chase. Supernatants were collected and cells lysed in NP40 lysis buffer (Selby et al., *Virology* (1994) 204:114–122). Cleared supernatants and lysates were incubated with protein A SEPHAROSE™-bound rabbit anti-sAg serum (Accurate Chemicals, Westbury, N.Y.) that was previously blocked 1 h with unlabelled CHO cell supernatant or lysate.

Analysis of transcripts for ordered linkage: For each assay, total RNA from approximately 5×10⁶ phosphate-buffered saline-washed cells was isolated by lysing cells in 1 ml RNA-STAT 60 (Tel-Test B, Inc., Friendswood, Tex.) and extracting once with CHCl₃ followed by isopropanol precipitation. Random-primed reverse transcription reactions were performed using the GENEAMP™ RNA PCR kit (Perkin Elmer/Roche Molecular Systems, Branchburg, N.J.) substituting the kit RT enzyme with MuMLV RT (200 μ/ml) (BRL). PCR-amplification of the CMV-promoter-preS2 junction was done using primers 126 and 127; for the preS2-EMCV leader junction primers 128 and 129. For an internal control, reverse transcription and PCR amplification of the actin gene using primers AW75 and AW76 was done. Junction products were sequenced for comparison to the input fragment sequences.

Results

As explained above, dhfr-negative CHOdg44 cells were transfected with three individual DNA elements: (i) a HindIII-Sal1 fragment from pCMVII (see FIGS. 1 and 2), containing the human CMV promoter with a short spacer incorporated between exon 2 of the CMV immediate early transcription unit and the Sal1 cloning site; (ii) PCR-amplified DNA coding for the HBV PreS2 gene including 5 base pair spacers located between the terminal nucleotides of the gene and the terminal Sal1 and Nhe1 restriction enzyme sites of the fragment (FIG. 2); and (iii) an Xba1-Not1 fragment from pET-E-DHFR/Neo$_{(m2)}$BGHt containing the EMCV-DHFR/Neo$_{(m2)}$ selection cassette (FIGS. 1 and 2).

Figure 3:
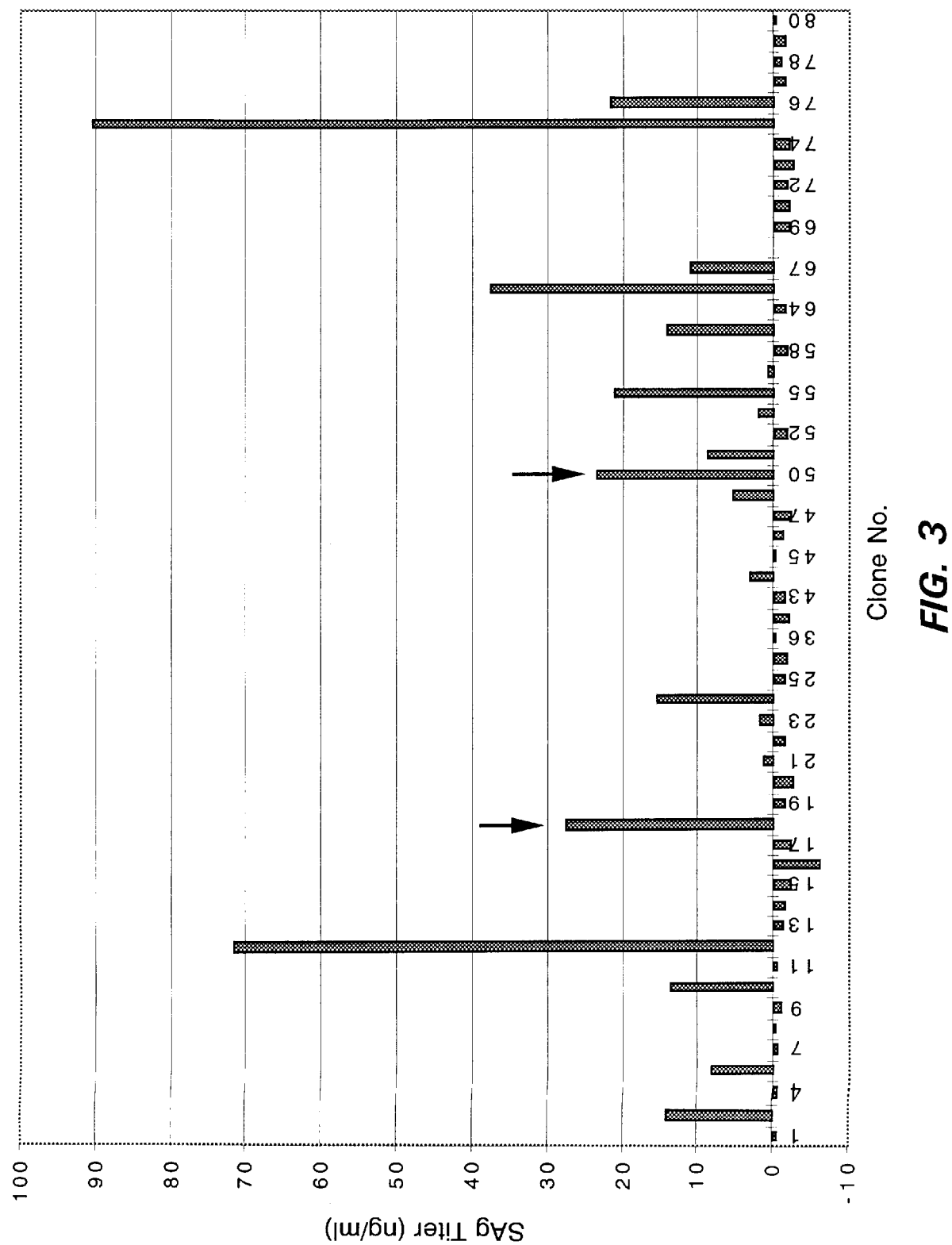
FIG. 3 shows sAg titers of from cells transfected as shown in FIG. 2, prior to methotrexate (Mtx) amplification in dhfr selective medium. The arrows indicate clones subsequently subjected to Mtx selection, as described in the examples.

Approximately 100 geneticin-resistant, DHFR⁺ clones were picked and analyzed for sAg expression. Initial titers ranged from 0–90 ng/ml (average was 30 ng/ml) (FIG. 3). A subset of clones showing relatively higher initial expression were further expanded. Two of those that continued to show high expression after further expansion, T21.18 and T21.50 (the parental clones, indicated with arrows in FIG. 3), were shown to contain preS2 genes of correct sequence as determined by sequencing of RT-PCR products generated from total cellular RNAs. This analysis showed that for both clones, nucleotide sequence changes relative to the predicted sequence were introduced in the junctional regions at either end of the preS2 gene. However, none of these changes interfered with the splice acceptor site of exon2 that lies adjacent to the 3' terminus of the CMV promoter fragment, nor did any of the changes alter the sequence of the preS2 gene itself.

These two clones were subsequently subjected to a single round of methotrexate selection at 20, 50, and 100 nM drug concentrations.

Figure 4A:
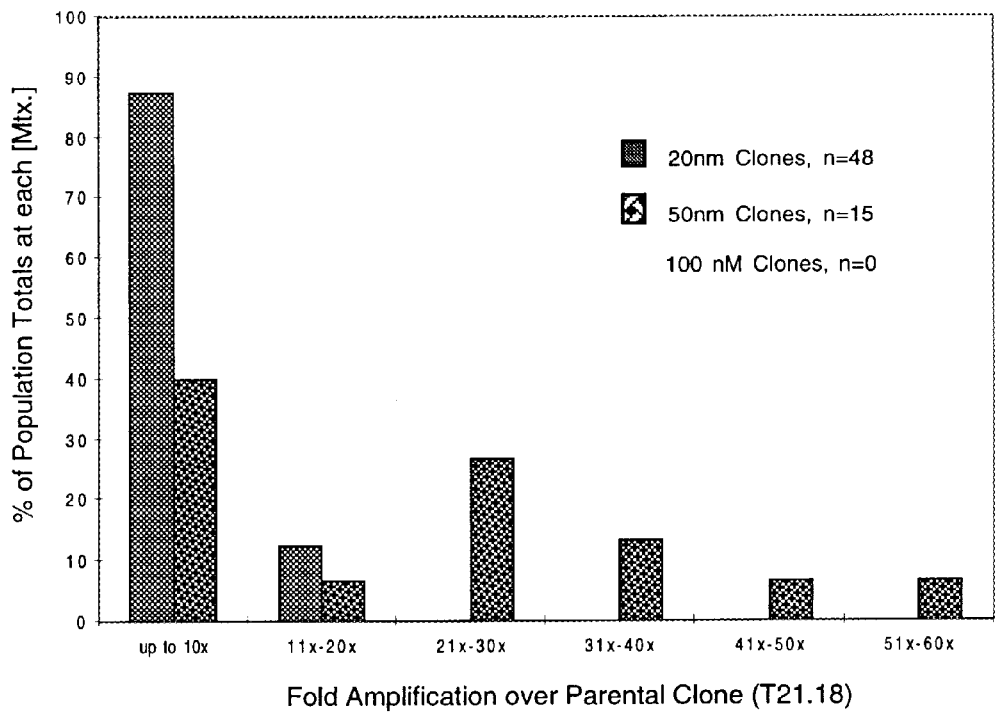
FIGS. 4A and 4B depict amplification results for subclones T21.18 (FIG. 4A) and T21.50 (FIG. 4B), as described in the examples.
Figure 4B:
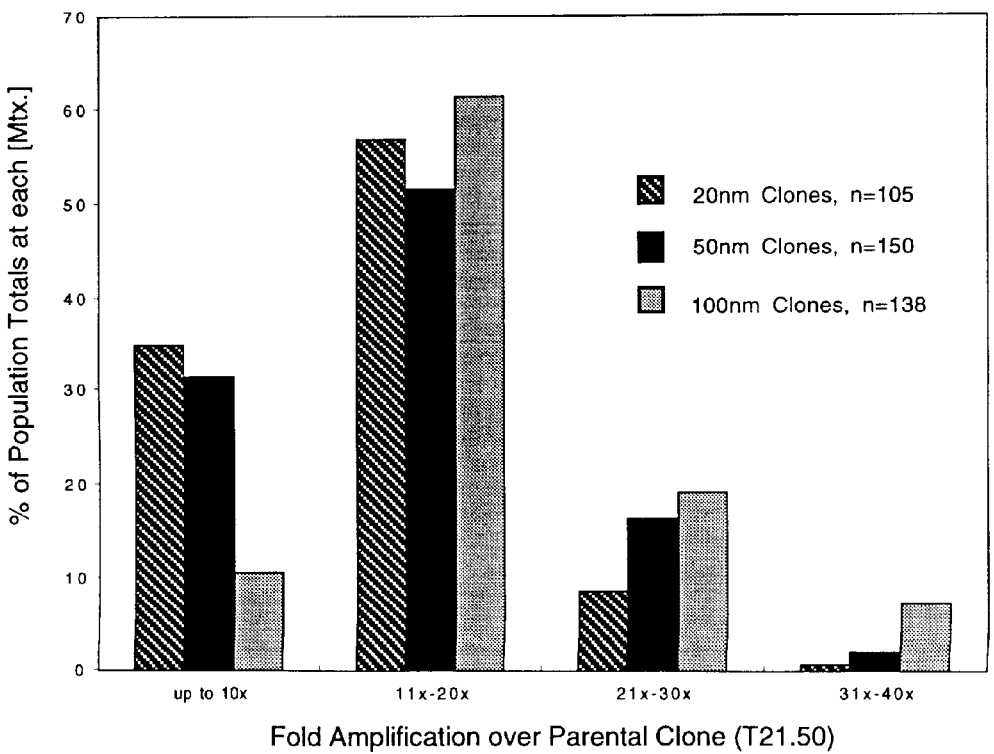

As shown in FIGS. 4A and 4B, an unprecedented range of amplifications were observed for both parental clones. For each, the majority of subclones arising from selection showed up to a twenty-fold enhancement of sAg expression relative to the starting parental clone titers. While this level of amplification is very impressive in comparison to the two to ten-fold amplifications that are more typically seen using standard selection vectors, even more impressive are the subset of clones that showed amplification of up to sixty-fold over the parental clones. This was most evident for those selected in 50 and 100 nM methotrexate. In the case of the T21.50-derived selectants, a direct relationship was observed between drug concentration and the percentage of clones showing amplification in the range of twenty to forty-fold, suggesting that there is potential efficiency gained by selecting at higher drug concentrations.

Figure 5:
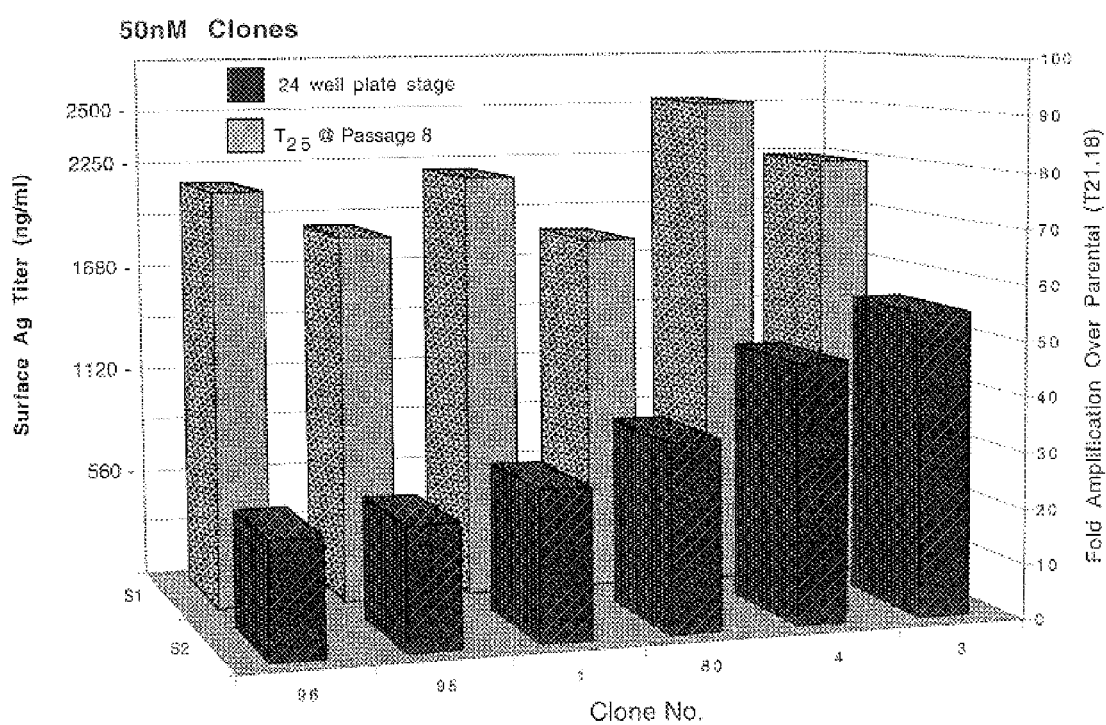
FIG. 5 shows sAg titers from subclones derived from the T21.18 parental clone following extended passaging, as described in the examples. The degree of amplification over the parental clones is also shown.

Based on the observation that continued passage of high expressors can result in a "stabilizing" of expression, often at higher than initial levels, a number of the highest expressing clones from each set were passaged 6–8 times in T-flasks, then reassayed for sAg expression. On the whole, the titers rose, with one clone (T21.18.4) showing an extraordinary ninety-fold amplification as compared to the preamplification titer of the parental clone (see FIG. 5). This level of amplification represents expression in the range of 6 mg(est.)/10⁹ c/day.

Figure 6:
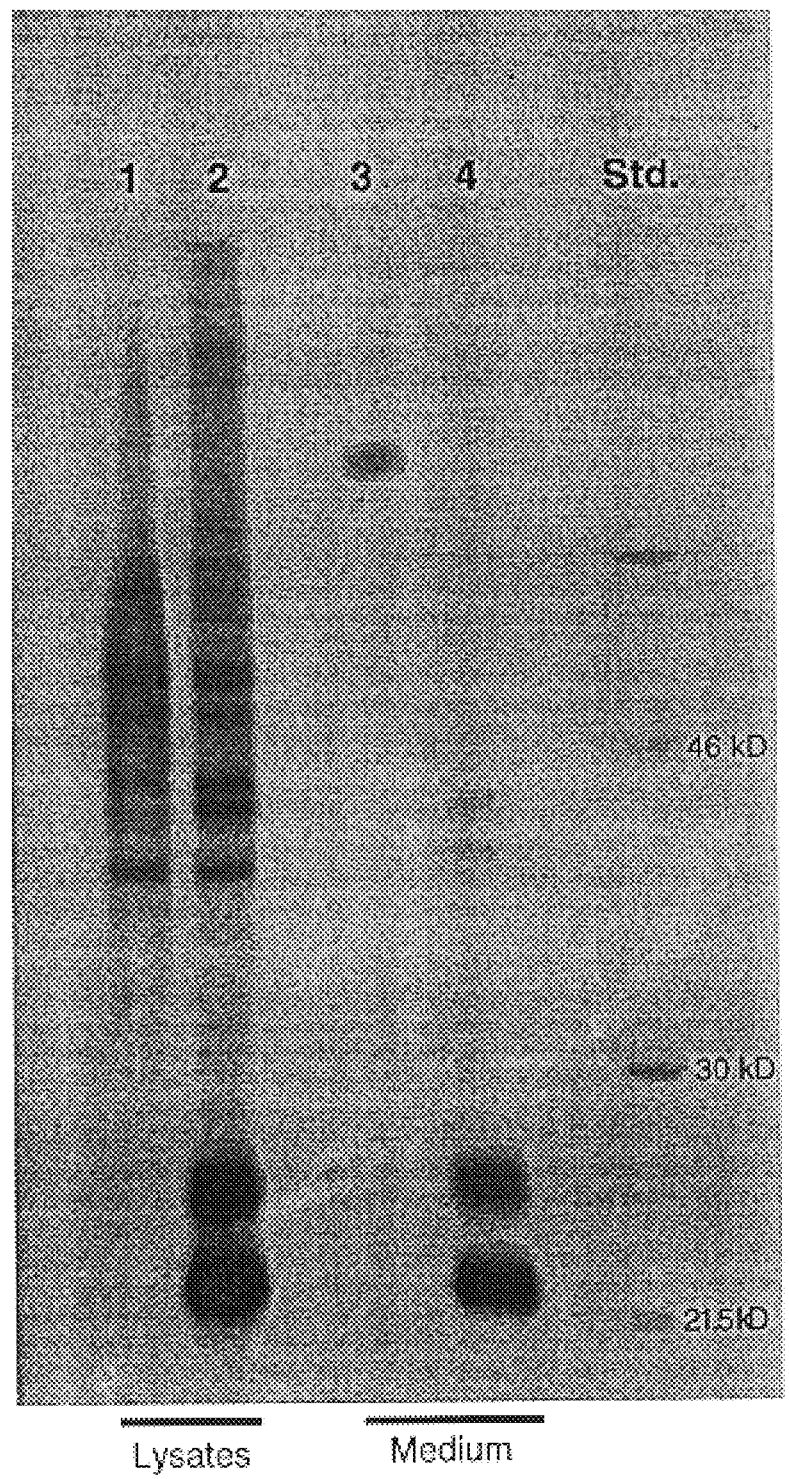
FIG. 6 shows the results of an immunoprecipitation experiment using rabbit anti-HBV sAg. Labelled cell lysates or culture medium from subclone T21.18.25 cells (lanes 2 and 4) or control CHOdg44 cells (lanes 1 and 3) were immunoprecipitated as described in the examples.

To verify that authentic preS2 and sAg proteins were being made by these recombinant cell clones, one of the highest expressing clones (T21.18.25) was radiolabelled and proteins from the culture medium and cell lysates were immunoprecipitated using sAg-specific polyclonal sera. As shown in FIG. 6, glycosylated and unglycosylated versions of sAg and preS2 were found in the cell lysates and culture medium. The sizes of the precipitated proteins, p24, gp27, p36, and gp39 corresponded well to the expected sizes of unglycosylated/glycosylated sAg and unglycosylated/glycosylated preS2, respectively.

Accordingly, novel noncloning methods for recombinantly producing proteins are disclosed. Although preferred embodiments of the subject invention have been described in some detail, it is understood that obvious variations can be made without departing from the spirit and the scope of the invention as defined by the appended claims.

What is claimed is:

1. A method of expressing at least one recombinant polypeptide comprising:
   (a) providing as separate elements (i) a first nucleic acid element which comprises a promoter, (ii) a second nucleic acid element which comprises at least one selectable marker gene conferring a selectable phenotype on a cell transfected therewith, an internal ribosome entry site (IRES) sequence positioned upstream of the selectable marker gene, and a transcription termination sequence positioned downstream of the selectable marker gene, and (iii) a third nucleic acid element which comprises at least one gene encoding said at least one polypeptide;
   (b) cotransfecting a population of mammalian cells with each of said first, second and third elements;
   (c) culturing said population of cells under conditions whereby the polypeptide and the at least one selectable marker are expressed;
   (d) selecting cells which express the selectable marker; and
   (e) identifying those cells from the selected cells that express the recombinant polypeptide.

2. The method of claim 1, wherein the promoter is the human cytomegalovirus (CMV) immediate-early enhancer/promoter and includes the CMV intron A.

3. The method of claim 1, wherein the at least one selectable marker gene comprises a dhfr gene.

4. The method of claim 1, wherein the IRES sequence is derived from encephalomyocarditis virus.

5. The method of claim 1, wherein the third nucleic acid element is a cDNA library.

6. The method of claim 1, wherein the third nucleic acid element is a PCR product.

7. The method of claim 1, wherein the third nucleic acid element is from a DNA virus.

8. The method of claim 1, wherein the gene of the third nucleic acid element is bounded on its 5' end with a nucleotide sequence of about 3 to about 150 nucleotides complementary to the 3' end of the first nucleic acid element, and bounded on its 3' end with a nucleotide sequence of about 3 to about 150 nucleotides, complementary to the 5' end of the second nucleic acid element.

9. The method of claim 1, wherein the at least one selectable marker gene comprises a neo$^r$ gene.

10. The method of claim 9, wherein the neo$^r$ gene is neo$_{(m2)}$ which confers reduced resistance to geneticin on a cell transfected therewith as compared to the wild-type neo$^r$ gene.

11. The method of claim 1, wherein the polypeptide encoded by the third nucleic acid element is a viral protein.

12. The method of claim 11, wherein the viral protein is a hepatitis virus protein.

13. The method of claim 12, wherein the hepatitis protein is a hepatitis B virus (HBV) protein.

14. The method of claim 13, wherein the HBV protein is HBV preS2.

15. A method of expressing at least one recombinant polypeptide comprising:
   (a) providing as separate elements (i) a first nucleic acid element which comprises a promoter, (ii) a second nucleic acid element which comprises at least one selectable marker gene selected from the group consisting of a neo$^r$ gene and a dhfr gene, an encephalomyocarditis virus (EMCV) internal ribosome entry site (IRES) sequence positioned upstream of the selectable marker gene, and a transcription termination sequence positioned downstream of the selectable marker gene, and (iii) a third nucleic acid element which comprises at least one gene encoding said at least one polypeptide, wherein the gene is bounded on its 5' end with a nucleotide sequence of about 3 to about 150 nucleotides complementary to the 3' end of the first nucleic acid element, and bounded on its 3' end with a nucleotide sequence of about 3 to about 150 nucleotides, complementary to the 5' end of the second a nucleic acid element;
   (b) cotransfecting a population of mammalian cells with each of said first, second and third elements;
   (c) culturing said population of cells under conditions whereby the polypeptide and the at least one selectable marker are expressed;
   (d) selecting cells which express the selectable marker; and
   (e) identifying those cells from the selected cells that express the recombinant polypeptide.

16. The method of claim 15, wherein the promoter is the human cytomegalovirus (CMV) immediate-early enhancer/promoter and includes the CMV intron A.

17. The method of claim 15, wherein the neo$^r$ gene is NEO$_{(m2)}$ which confers reduced resistance to geneticin on a cell transfected therewith as compared to the wild-type neo$^r$ gene.

18. The method of claim 15, wherein the third nucleic acid element is a cDNA library.

19. The method of claim 15, wherein the third nucleic acid element is a PCR product.

20. The method of claim 15, wherein the third nucleic acid element is from a DNA virus.

21. The method of claim 15, wherein the second nucleic acid element comprises both a neo$^r$ gene and a dhfr gene.

22. The method of claim 21, wherein the neo$^r$ gene is positioned downstream of the dhfr gene.

23. The method of claim 22, wherein the stop codon for the dhfr gene is replaced with a spacer of about 3 to about 150 nucleotides, such that transcription and translation of both the dhfr and $neo^r$ genes occurs.

24. The method of claim 23, wherein the spacer is about 12 to about 18 nucleotides.

25. The method of claim 15, wherein the polypeptide encoded by the third nucleic acid element is a viral protein.

26. The method of claim 25, wherein the viral protein is a hepatitis virus protein.

27. The method of claim 26, wherein the hepatitis protein is a hepatitis B virus (HBV) protein.

28. The method of claim 27, wherein the HBV protein is HBV preS2.

29. A selectable marker nucleic acid element comprising: (a) a $neo^r$ gene, (b) a dhfr gene positioned upstream of the $neo^r$ gene, wherein the stop codon for the dhfr gene is replaced with a spacer of about 3 to about 150 nucleotides, such that transcription and translation of both the dhfr and $neo^r$ genes occurs, (c) an internal ribosome entry site (IRES) sequence positioned upstream of the dhfr gene, (d) and a transcription termination sequence positioned downstream of the $neo^r$ gene.

30. The selectable marker element of claim 29, wherein the $neo^r$ gene is $NEO_{(m2)}$ which confers reduced resistance to geneticin on a cell transfected therewith as compared to the wild-type $neo^r$ gene.

31. The selectable marker element of claim 29, wherein the IRES sequence is derived from encephalomyocarditis virus.

32. The selectable marker element of claim 29, wherein the transcription termination sequence is a bovine growth hormone transcription termination sequence.

33. The selectable marker element of claim 29, wherein the spacer is about 12 to about 18 nucleotides.

34. A mammalian host cell transfected with the selectable marker nucleic acid element of claim 29.

35. A selectable marker nucleic acid element comprising: (a) a $neo^r$ gene is $NEO_{(m2)}$ which which confers reduced resistance to geneticin on a cell transfected therewith as compared to the wild-type $neo^r$ gene, (b) a dhfr gene positioned upstream of the $neo^r$ gene, wherein the stop codon for the dhfr gene is replaced with a spacer of about 12 to about 18 nucleotides, such that transcription and translation of both the dhfr and $neo^r$ genes occurs, (c) an encephalomyocarditis virus internal ribosome entry site (IRES) sequence positioned upstream of the dhfr gene, (d) and a bovine growth hormone transcription termination sequence positioned downstream of the $neo^r$ gene.

36. A mammalian host cell transfected with the selectable marker nucleic acid element of claim 35.

* * * * *

SEQUENCE LISTING

<160> NUMBER OF SEQ ID NOS: 20

<210> SEQ ID NO 1
<211> LENGTH: 29
<212> TYPE: DNA
<213> ORGANISM: Artificial Sequence
<220> FEATURE:
<223> OTHER INFORMATION: Description of Artificial Sequence: preS2
      primer 83

<400> SEQUENCE: 1
gtcgacgaca gatgcagtgg aattccact                              29

<210> SEQ ID NO 2

```
<211> LENGTH: 32
<212> TYPE: DNA
<213> ORGANISM: Artificial Sequence
<220> FEATURE:
<223> OTHER INFORMATION: Description of Artificial Sequence:  preS2
      primer 84

<400> SEQUENCE: 2
gctagcgcag attaaatgta tacccagaga ca                                      32

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: mutant
      neo primer 91

<400> SEQUENCE: 3
tcagaagaac tcgttaagaa                                                    20

<210> SEQ ID NO 4
<211> LENGTH: 16
<212> TYPE: DNA
<213> ORGANISM: Artificial Sequence
<220> FEATURE:
<223> OTHER INFORMATION: Description of Artificial Sequence: mutant
      neo primer 93

<400> SEQUENCE: 4
ttgaacaaga tggatt                                                        16

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: DHFR
      primer 38

<400> SEQUENCE: 5
ccatggttcg accattggaa                                                    20

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence: DHFR
      primer 75

<400> SEQUENCE: 6
ggatccccgc cgtctttctt ctcgta                                             26

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: CMVp-preS2
      RT-PCR primer 126

<400> SEQUENCE: 7
gggaacggtg cattggaa                                                      18

<210> SEQ ID NO 8
<211> LENGTH: 17
```

```
<212> TYPE: DNA
<213> ORGANISM: Artificial Sequence
<220> FEATURE:
<223> OTHER INFORMATION: Description of Artificial Sequence:  CMVp-preS2
      RT-PCR primer 127

<400> SEQUENCE: 8
ccctgactct gggatcc                                                      17

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence:  CMVp-preS2
      RT-PCR primer 95

<400> SEQUENCE: 9
ccacgctgtt ttgacctc                                                     18

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: CMVp-preS2
      RT-PCR primer 96

<400> SEQUENCE: 10
ccgtactggt tgttgttga                                                    19

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: preS2-EMCV
      primer 128

<400> SEQUENCE: 11
cgtgagtccc tttataccg                                                    19

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: preS2-EMCV
      primer 129

<400> SEQUENCE: 12
cggccagtaa cgttaggg                                                     18

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence: preS2-EMCV
      primer 98

<400> SEQUENCE: 13
tatagacaaa cgcacaccg                                                    19

<210> SEQ ID NO 14
<211> LENGTH: 18
<212> TYPE: DNA
```

```
<213> ORGANISM: Artificial Sequence
<220> FEATURE:
<223> OTHER INFORMATION: Description of Artificial Sequence: preS2-EMCV
      primer 123

<400> SEQUENCE: 14
aaccagtacg ggaccatg                                                    18

<210> SEQ ID NO 15
<211> LENGTH: 12
<212> TYPE: DNA
<213> ORGANISM: Artificial Sequence
<220> FEATURE:
<221> NAME/KEY: CDS
<222> LOCATION: (1)..(12)
<220> FEATURE:
<223> OTHER INFORMATION: Description of Artificial Sequence: Flexible Hinge
      Sequence (Fig. 1)

<400> SEQUENCE: 15 gga gga gga tcc                                                        12
Gly Gly Gly Ser
  1

<210> SEQ ID NO 16
<211> LENGTH: 4
<212> TYPE: PRT
<213> ORGANISM: Artificial Sequence
<220> FEATURE:
<223> OTHER INFORMATION: Description of Artificial Sequence: Flexible
      Hinge Sequence (Fig. 1)

<400> SEQUENCE: 16

Gly Gly Gly Ser
  1

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence:
      Spacer-Containing Sequence (Fig. 1)

<400> SEQUENCE: 17
ctgcagtcac cgtcagctcg tcgac                                            25

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence:
      Spacer-Containing Sequence (Fig. 2)

<400> SEQUENCE: 18
gtcgacgaca gatgcagtgg                                                  20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence:
      Spacer-Containing Sequence (Fig. 2)

<400> SEQUENCE: 19
tacatttaat ctgcgctagc                                                  20
```

```
<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: Flexible
      Hinge-Containing Sequence (Fig. 2)

<400> SEQUENCE: 20
aaagacggag gaggatccat gatt                                              24
```